(12) United States Patent
Davison

(10) Patent No.: US 8,246,821 B2
(45) Date of Patent: Aug. 21, 2012

(54) CHROMATOGRAPHIC SOLVENT MONITOR

(75) Inventor: Dale A. Davison, Greenwood, NE (US)

(73) Assignee: Teledyne Instruments, Inc., Thousand Oaks, CA (US)

( * ) Notice: Subject to any disclaimer, the term of this patent is extended or adjusted under 35 U.S.C. 154(b) by 911 days.

(21) Appl. No.: 12/221,510

(22) Filed: Aug. 4, 2008

(65) Prior Publication Data

US 2008/0296207 A1 Dec. 4, 2008

Related U.S. Application Data

(62) Division of application No. 11/074,880, filed on Mar. 8, 2005, now Pat. No. 7,419,598.

(51) Int. Cl.
*B01D 15/08* (2006.01)

(52) U.S. Cl. ........ 210/198.2; 210/656; 210/86; 210/143

(58) Field of Classification Search .................. 210/656, 210/744, 86, 137, 143, 188, 198.2
See application file for complete search history.

(56) References Cited

U.S. PATENT DOCUMENTS

| | | |
|---|---|---|
| 4,034,607 A | 7/1977 | Martig |
| 4,081,998 A | 4/1978 | Martig |
| 4,083,246 A | 4/1978 | Marsh |
| 4,111,044 A | 9/1978 | McClure |
| 4,125,020 A | 11/1978 | McClure |
| 4,127,030 A | 11/1978 | Martig |
| 4,127,032 A | 11/1978 | Martig |
| 4,145,923 A | 3/1979 | McClure |
| 4,145,926 A | 3/1979 | Martig |
| 4,176,550 A | 12/1979 | McClure |
| 4,291,575 A | 9/1981 | Frissora |
| 4,299,116 A | 11/1981 | Baillie et al. |
| 4,388,827 A | 6/1983 | Palmer et al. |
| 4,393,451 A * | 7/1983 | Barker ........................... 702/47 |
| 4,437,812 A * | 3/1984 | Abu-Shumays et al. ....... 417/53 |
| 4,467,644 A | 8/1984 | Palmer et al. |
| 4,550,600 A | 11/1985 | Lindgren |
| 4,728,434 A * | 3/1988 | Trafford ........................ 210/656 |
| 4,747,062 A * | 5/1988 | Esau .............................. 702/55 |
| 4,772,157 A | 9/1988 | Obermeyer |

(Continued)

FOREIGN PATENT DOCUMENTS

JP 63 165720 7/1988

(Continued)

OTHER PUBLICATIONS

Snyder, Introduction to Modem Liquid Chromatography, 1979, pp. 88-90.*

*Primary Examiner* — Ernest G Therkorn

(74) *Attorney, Agent, or Firm* — Suiter Swantz pc llo

(57) ABSTRACT

A bubbler is positioned within a solvent reservoir of a chromatographic system with its opening near the bottom of the system to measure the pressure of solvent. The bubbler may use air or may use helium or some other gas so that the solvent can be purged of excess air while its level is being monitored by the bubbler. The bubbler provides a depth signal to a microcontroller that records the drop in pressure and projects a low level of pressure at which point solvent should be replenished. The microprocessor may provide a signal to the operator or terminate operation or automatically replenish solvent depending upon the program.

8 Claims, 4 Drawing Sheets

U.S. PATENT DOCUMENTS

| | | | |
|---|---|---|---|
| 4,981,597 A * | 1/1991 | Allington et al. | 210/656 |
| 5,038,840 A | 8/1991 | Fair | |
| 5,052,222 A | 10/1991 | Stoepfel | |
| 5,112,492 A * | 5/1992 | Ransohoff | 210/656 |
| 5,158,675 A * | 10/1992 | Allington et al. | 210/198.2 |
| 5,163,324 A | 11/1992 | Stewart | |
| 5,217,590 A * | 6/1993 | Lauer et al. | 204/453 |
| 5,234,587 A * | 8/1993 | Allington et al. | 210/198.2 |
| 5,279,338 A | 1/1994 | Goossens | |
| 5,280,721 A * | 1/1994 | Carson | 73/216 |
| 5,298,881 A * | 3/1994 | Bowman | 340/450.3 |
| 5,309,764 A | 5/1994 | Waldrop et al. | |
| 5,315,876 A | 5/1994 | Glassey et al. | |
| 5,407,569 A * | 4/1995 | Greenley et al. | 210/198.2 |
| 5,534,152 A * | 7/1996 | Schick | 210/656 |
| 5,625,344 A | 4/1997 | Shukla et al. | |
| 5,684,250 A | 11/1997 | Marsh et al. | |
| 5,691,914 A | 11/1997 | Randolph | |
| 6,334,337 B1 | 1/2002 | Macedo et al. | |
| 6,427,526 B1 * | 8/2002 | Davison et al. | 73/61.55 |
| 6,793,815 B2 * | 9/2004 | Hoffmann | 210/198.2 |
| 2003/0173272 A1 * | 9/2003 | Staffler | 210/87 |
| 2004/0000510 A1 * | 1/2004 | Hoffman | 210/101 |

FOREIGN PATENT DOCUMENTS

| | | |
|---|---|---|
| JP | 2002 277451 A | 9/2002 |

* cited by examiner

CHROMATOGRAPHIC SOLVENT MONITOR

REFERENCE TO RELATED APPLICATIONS

This application is a divisional of U.S. application Ser. No. 11/074,880 filed Mar. 8, 2005, filed in the name of Dale A. Davison for CHROMATOGRAPHIC SOLVENT MONITOR, now U.S. Pat. No. 7,419,598.

BACKGROUND OF THE INVENTION

This invention relates to liquid chromatographic methods and apparatuses and more particularly to methods and apparatuses for monitoring the solvent in a liquid chromatographic system.

Liquid chromatographic apparatuses that automatically monitor the solvent are known. This feature has become increasingly significant with the increasing use of flash chromatography, arrays of columns that use solvent from the same reservoir and automated unattended operation of the chromatographic systems. Such systems are monitored to avoid having the system run out of solvent in the middle of a chromatographic run and nonetheless continue operation of some parts of the system without one or more of the solvents required. The increased rate at which solvent is used and the ability of some systems to automatically increase the amount of solvent needed during a chromatographic run has resulted in systems unexpectedly running out of solvent during chromatographic runs. For example, some systems can increase the length of a chromatographic run without operator intervention, such as when the programmed time has elapsed but a peak is being detected.

One prior art system having the feature of monitoring the solvent during a chromatographic run tracks the amount of solvent used during a run in accordance with the program for the run and when the solvent is predicted to run out, terminates the chromatographic run. This system has several disadvantages, such as: (1) it requires that the operator correctly enter into the system the starting amount of solvent; (2) it requires operator intervention when the chromatographic system is terminated to replenish the solvent and reset the system; (3) it is more complicated than desired; and (4) it can fail to provide a warning ahead of time that the system needs to have solvent replenished when the run is automatically extended.

SUMMARY OF THE INVENTION

Accordingly, it is an object of the invention to provide a novel chromatographic system and method.

It is a still further object of the invention to provide a novel low-cost method for reliably providing substantial amounts of solvent to a chromatographic system.

It is a still further object of the invention to provide a novel system for avoiding running out of solvent before a chromatographic run is completed.

It is a still further object of the invention to provide a novel system for stopping a chromatographic run before the solvent is exhausted, which system is relatively simple and inexpensive.

It is a still further object of the invention to provide a novel system for monitoring solvent that does not require entering the correct amount of solvent into the controller before starting operation.

In accordance with the above and further objects of the invention, a chromatographic system includes as part of the system a solvent reservoir and a solvent level sensor. When the solvent is low, a solvent-level indicating signal is provided to the operator so that additional solvent can be added by the operator before the system runs out or additional solvent automatically is added. In the preferred embodiment, a bubbler is used to determine the depth of the solvent in a reservoir. The bubbler may also be used to purge the solvent of air and thus reduce the bubbles in the detector. For example, the gas used by the bubbler may be helium which will remove some air and avoid the introduction of air from an air-operated bubbler.

One unexpected difficulty with this system occurs because the same system is intended to be used with different solvents and in some circumstances, different shaped solvent reservoirs. This circumstance, if not compensated for, increases operator's involvement to adjust readings in accordance with the density of the solvent and the shape of the containers. However, in one embodiment, the signal from the bubbler or other pressure sensing instrument is used to compensate for possible changes to solvents with different densities and/or changes in the reservoir shape. This is accomplished by determining the rate of change of pressure signal with respect to the rate of usage of solvent as known from the programmed run. These two parameters can be used to determine the time at which the solvent will reach a level that predicts a possible exhaustion of solvent. This information can be provided to the operator or it can be used to automatically replenish the solvent.

It can be understood from the above description that the liquid chromatographic apparatus and technique of this invention has several advantages, such as: (1) it avoids having solvent run out during a chromatographic run, resulting in wasted solvent, a compromised column, lost sample and/or lost operator time; (2) it reduces the monitoring effort that must be supplied by persons operating the chromatograph; and (3) it is relatively inexpensive and can be implemented principally as software.

SUMMARY OF THE DRAWINGS

The above noted and other features of the invention will be better understood from the following detailed description when considered with reference to the accompanying drawings in which.

DETAILED DESCRIPTION

Figure 1:
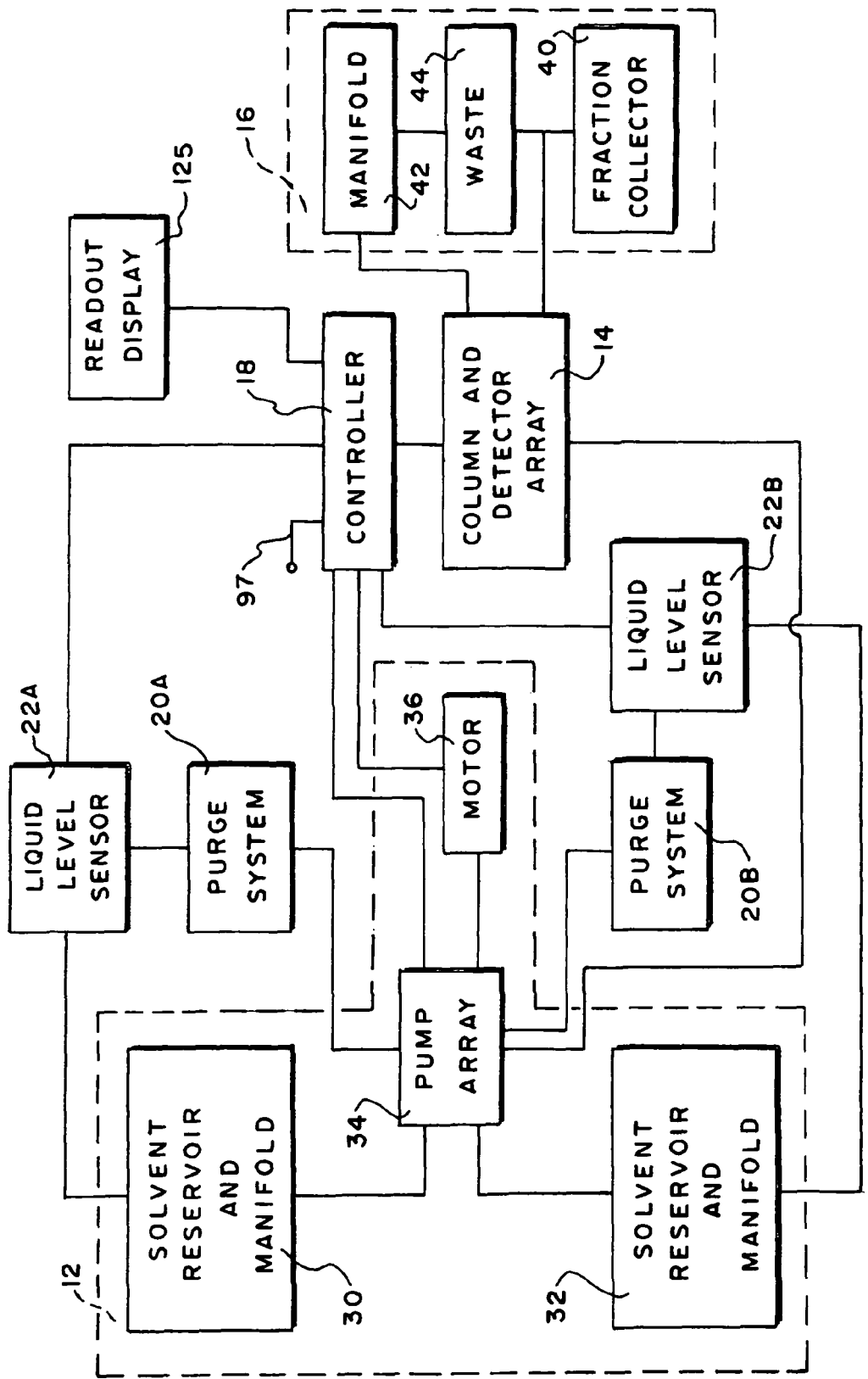
FIG. 1 is a block diagram of a liquid chromatographic system in accordance with an embodiment of the invention.

In FIG. 1, there is shown a block diagram of a preparatory liquid chromatographic system 10 having a pumping system 12, a column and detector array 14, a collector system 16, a controller 18, a purge system 20A and 20B and a liquid level sensor 22A and 22B. The pumping system 12 supplies solvent to the column and bands are sensed by a detector array 14 under the control of the controller 18. The purge system 20A and 20B communicates with a pump array 34 to purge the pumps and the lines between the pumps and the columns between chromatographic runs. The pump array 34 supplies solvent to the column and detector array 14 from which effluent flows into the collector system 16 under the control of the controller 18. The controller 18 receives signals from detectors in the column and detector array 14 indicating bands of solute and activates the fraction collector system 16 accordingly in a manner known in the art. One suitable fraction collection system is the FOXY® 200 fraction collector available from Isco, Inc., 4700 Superior Street, Lincoln, Nebr. 68504. A chromatographic system which may use the novel solvent monitor is described in greater detail in U.S. Pat. No. 6,427,526, to Davison, et al., the disclosure of which is incorporated by reference.

To detect if solvent in either of solvent reservoirs within solvent reservoir and manifold 30 or 32 is running low, the liquid level sensors 22A and 22B are in communication with the solvent reservoir and manifold 30 and the solvent reservoir and manifold 32 respectively to receive signals indicating the pressure near the bottom of the reservoirs 30 and 32 and to supply that information to the controller 18 to which each of them is electrically connected. In the preferred embodiment, the liquid level sensors are bubblers which have Teflon tubing or other tubing that is compatible with the solvent extending to the bottom of the reservoirs to measure the pressure at the bottom of the reservoirs. The use of bubblers is advantageous since they are inexpensive and only the tubing, which can be selected for compatibility with the solvent extends into the reservoir. They may operate from a gas supply which, in some embodiments, may operate the purge systems 20A and 20B as well. A suitable bubbler is disclosed in U.S. Pat. No. 5,280,721 to Douglas T. Carson, the disclosure of which is incorporated by reference although many bubblers are available on the market and are suitable for use in this invention.

Generally, the bubblers will operate from an air supply that may also be used in the purge system. However, an additional benefit can be obtained by using helium or other suitable gas in the bubbler. This will permit the gas escaping from the end of the tubing in the bubbler to also remove air or moisture or other undesirable substances within the reservoir. For example, helium is commonly used to remove air from solvent.

To supply solvent to the pump array 34, the pumping system 12 includes a plurality of solvent reservoirs and manifolds, a first and second of which are indicated at 30 and 32 respectively, a pump array 34 and a motor 36 which is driven under the control of the controller 18 to operate the array of pumps 34. The controller 18 also controls the valves in the pump array 34 to control the flow of solvent and the formation of gradients as the motor 36 actuates pistons of the reciprocating pumps in the pump array 34 simultaneously to pump solvent from a plurality of pumps in the pump array 34 and to draw solvent from the solvent reservoirs and manifolds such as 30 and 32. Valves in the pump array 34 control the amount of liquid, if any, and the proportions of liquids from different reservoirs in the case of gradient operation that are drawn into the pump and pumped from it. The manifolds communicate with the reservoirs so that a plurality of each of the solvents such as the first and second solvents in the solvent reservoir manifold 30 and 32 respectively can be drawn into the array of pumps 34 to permit simultaneous operation of a number of pumps. In some embodiments, the controller 18 may provide a signal on conductor 97 to cause solvent to flow from a large source of solvent into individual reservoirs that are low on solvent. In some embodiments, the controller 18 stops the run when a low level signal is received or causes the read-out display 125 to indicate a low solvent level.

While in the preferred embodiment, arrays of pumps, columns and detectors are used, any type of pump, column or detector is suitable. A large number of different liquid chromatographic systems are known in the art and to persons of ordinary skill in the art and any such known system may be adaptable to the invention disclosed herein with routine engineering. While two solvents are disclosed in the embodiment of FIG. 1, only one solvent may be used or more than two solvents.

To process the effluent, the collector system 16 includes a fraction collector 40 to collect solute, a manifold 42 and a waste depository 44 to handle waste from the manifold 42. One or more fraction collectors 40 communicate with the column and detector array 14 to receive the solute from the columns, either with a manifold or not. A manifold 42 may be used to combine solute from more than one column and deposit them together in a single receptacle or each column may deposit solute in its own receptacle or some of the columns each may deposit solute in its own corresponding receptacle and others may combine solute in the same receptacles. The manifold 42 communicates with the column and detector array 14 to channel effluent from each column and deposit it in the waste depository 44. The fraction collector 40 may be any suitable fraction collector such as that disclosed in U.S. Pat. No. 3,418,084 or the above-identified FOXY fraction collector.

Figure 2:
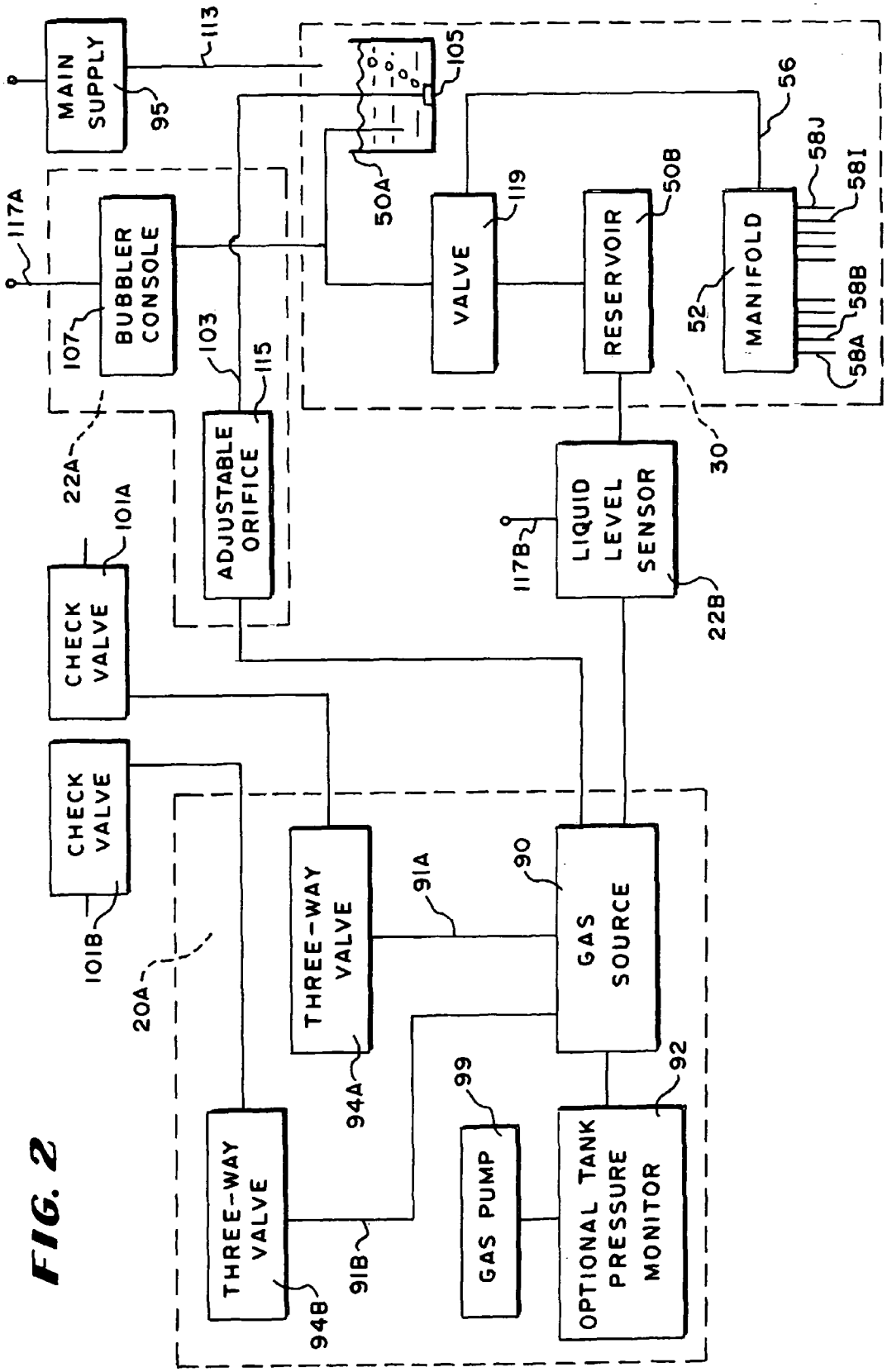
FIG. 2 is a flow diagram of a process of controlling a run in accordance with the invention.

In FIG. 2, there is shown a block diagram of a purge system 20A, a liquid level sensor 22A, 22B, and the solvent reservoir and manifold 30. In FIG. 1, two such identical systems are used but for clarity only one will be described herein. As explained in conjunction with FIG. 1, the purge system 20A supplies gas to any of a plurality of liquid level sensors, liquid level sensors 22A and 22B being shown in FIG. 2 for illustration. Each of the liquid level sensors 22A and 22B communicates with a different reservoir and with the controller 18 (FIG. 1) to monitor the solvent level in a corresponding reservoir. Several reservoirs may be associated with a single manifold so that different solvents may be utilized in chromatographic runs by operation of a valve with purge operation occurring between runs. Thus, different reservoirs with different solvents in them may be selected easily. In a simplified system, only one reservoir would be utilized with a single solvent. In any of the systems, the reservoirs may communicate with a large source of solvent and a signal indicating a low solvent level, instead of only informing the operator, could cause a replenishment of solvent into the reservoir from a larger supply or a main supply 95 illustrated with respect to reservoir 50A in FIG. 2.

In one embodiment, the purge system 20A includes a gas source 90, a plurality of three-way valves, two of which are shown at 94A and 94B, a tank pressure monitor 92 and a gas pump 99. The gas source 90 may be a reservoir which is supplied by the gas pump 99 and may contain air or in some embodiments, helium. In a simplified version, the gas pump 99 alone pumps air that may or may not be utilized to supply air for purging purposes. A simple diaphragm pump without pressure regulation or a reservoir may be adequate for some applications. For a more reliable operation, the tank pressure monitor 92 is connected to the gas source 90 and controls the pressure of the gas in the gas source 90 so that the purge operation may be done reliably at a selected gas pressure and more significantly, the gas pressure used in the bubblers may be reliably controlled. The embodiment shown in FIG. 2 has the gas pump 99 communicating through the tank pressure monitor 92 with the gas source 90 which is a gas reservoir to maintain a reliable preset gas pressure in the gas source. The gas source is then connected to the liquid level sensors, two of which are shown at 22A and 22B. In the preferred embodiment, the liquid level sensors are bubblers and the gas source supplies gas to the bubblers for the purpose of sensing the amount of solvent in the reservoirs. A plurality of three-way valves, valves 94A and 94B being shown by way of example in FIG. 2, may communicate with the gas source 90 to receive gas and, in one position of the three-way valve, supply it to purge systems through corresponding ones of check valves 101A and 101B.

The liquid level sensor 22A includes an adjustable or fixed orifice 115 connected to the gas source 90 to supply a continuous flow of air through tubing 103 to the bottom of reservoir 50A to cause bubbles to flow from the outlet at 105 of the tubing 103 against the pressure of liquid 54 at the bottom of the reservoir 50A. A transducer in the bubbler console 107 provides a signal indicating the pressure needed to maintain the air flow from the head of solvent in the reservoir. This signal may be used by the controller 18 (FIG. 1) to indicate when solvent is low and the system should be stopped or the solvent should be automatically replenished by main supply 95 and/or a message provided to the operator in a display on the controller 18 (FIG. 1). The signal representative of the pressure as measured by the bubbler console 107 is supplied to the controller 18 (FIG. 1) through a conductor 117A to indicate the level of the solvent in reservoir 50A. The second liquid level sensor 22B functions in the same manner as the first liquid level sensor 22A and is shown only generally in FIG. 2.

In one embodiment, the solvent reservoir and manifold 30 utilizing more than one reservoir with the more than one solvent as indicated at reservoirs 50A and 50B includes a valve 119 communicating with all of the reservoirs, two of which are shown at 50A and 50B as well as with manifold 52 and the liquid level sensor 22B so that the valve 119 receives fluid from the plurality of reservoirs, two of which are shown at 50A and 50B containing different solvents and selects one of them for application to the manifold 52. Each of the reservoirs such as 50A and 50B is connected to a corresponding liquid level sensor such as 22A or 22B, which in turn provides signals to the controller 18 through their electrical outlets 117A and 177B respectively.

The first solvent reservoir and manifold 30 includes a first manifold 52 having one inlet and ten outlets 58A-58J, a conduit 56 and a first solvent reservoir 50A, which solvent reservoir 50A holds a first solvent 54. The conduit 56 communicates with the solvent 54 in the solvent reservoir 50A through the valve 119 on one end and communicates with the interior of the manifold 52 at its other end. Each of the outlets 58A-58J of the manifold 52 communicate with the interior of a different one of ten cylinders of the pumps (not shown in FIG. 2) through appropriate valves. Similarly, the second manifold (FIG. 1) communicates with a second solvent in a second solvent reservoir through a another conduit. The second manifold also includes a plurality of outlet conduits that communicate with the interiors of a corresponding number of pump cylinders through appropriate valves as described in more detail in the aforesaid U.S. Pat. No. 6,427,526, to Davison, et al., so that the solvent from the reservoir 50A and the solvent from the second reservoir may be mixed together in a proportion that is set in accordance with the timing of the valves.

The check valves 101A and 101B communicate with purge manifolds (not shown in FIG. 2) to provide communication with the gas source 90 through conduits 91A, and 91B and the pressure monitor 92 and the three-way valves 94A and 94B to maintain an appropriate pressure for purging the lines. These purge manifolds each have ten outlets, each communicating with a different one of the ten conduits connecting a corresponding one of the corresponding pumps to a corresponding one of ten corresponding columns to transmit gas back through the piston pumps to purge the cylinders of the piston pumps and the conduits connecting the pumps to the columns. Each of the conduits connected to the purge connector arrangement lead to a corresponding pump in the pump array 34 (FIG. 1) which in turn communicates with the corresponding one of the columns in the column and detector array 14 (FIG. 1). Between chromatographic runs, the pressurized gas source 90, which is commonly a source of air, nitrogen or helium gas, communicates through the pressure regulator 92 and the three-way valves 94A, and 94B with the manifold to provide purging fluid to each of the corresponding outlets for each of the pump and column combinations.

While in the embodiment shown in FIG. 2 as an example, the manifolds each have ten outlet conduits which communicate with ten pump cylinders through appropriate valves as will be described hereinafter, each could have more or less than ten outlets and a manifold is not required for many chromatographic systems in which this novel solvent monitoring system has utility. Each of the reservoirs in the embodiment of FIG. 2 is similar to the reservoir 30 and operates in a similar manner to provide the same solvent from the same reservoir to a plurality of pump cylinders for simultaneous pumping of the solvent into a plurality of columns and therefore only one is shown in detail in FIG. 2 for simplicity.

Figure 3:
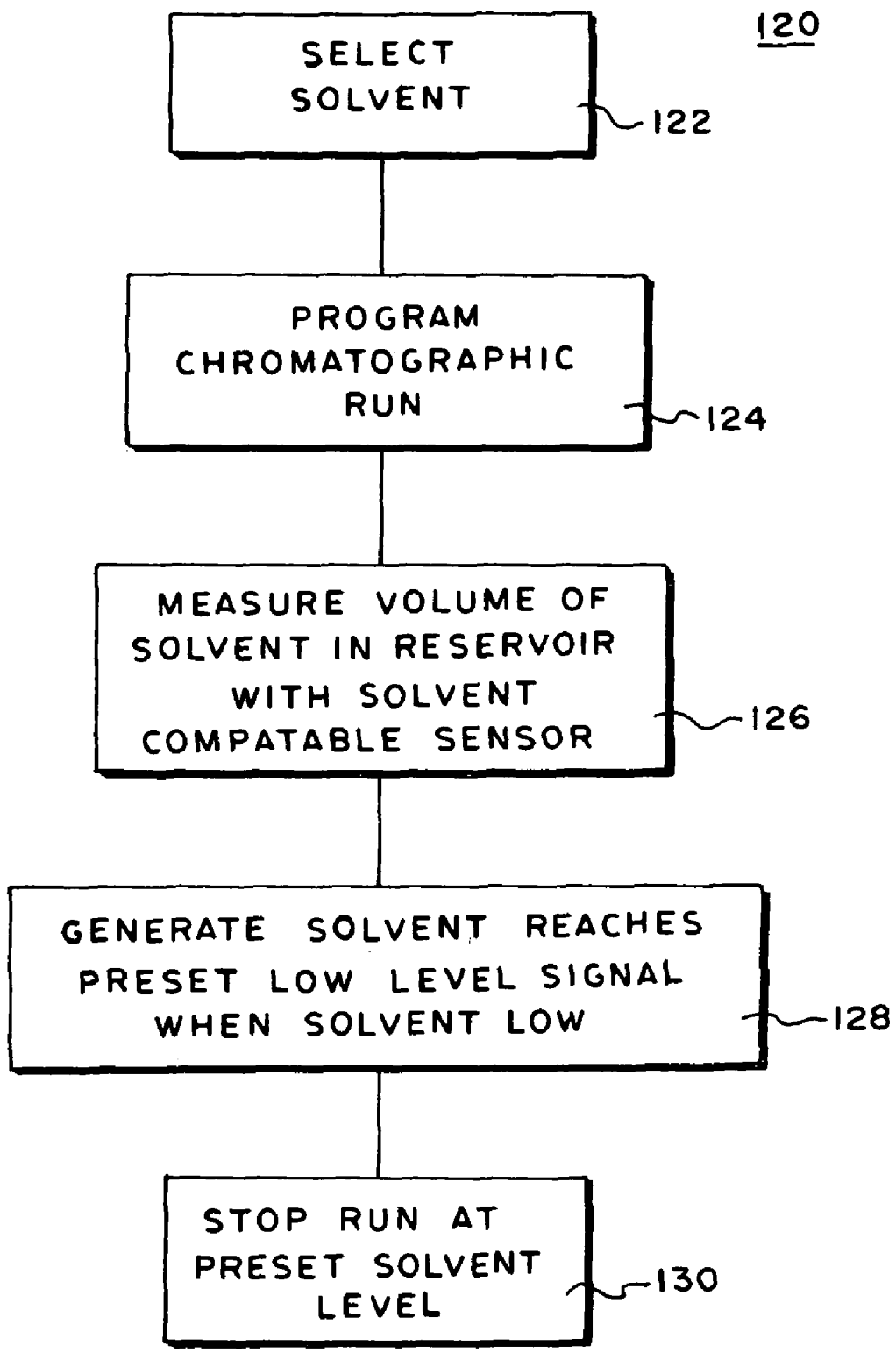
FIG. 3 is a flow diagram of the operation of the solvent monitoring technique useful in the embodiment of FIG. 1.

In FIG. 3, there is shown a flow diagram 120 of the operation of the solvent monitoring technique having the step of selecting a solvent 122, the step of programming a chromatographic run 124, the step 126 of measuring the volume of solvent in the reservoir with a solvent compatible sensor, the step 128 of generating a solvent level indicator signal when the solvent is low and the step 130 of stopping the chromatographic run at a preset solvent level. With this process, in some embodiments, a particular solvent may be selected as shown at step 122 from selection valves which connect different solvent reservoirs through a multi-position valve to supply fluid from any of the reservoirs into the system. Each of the reservoirs has associated with it a solvent monitoring system, which in the preferred embodiment, includes a bubbler to sense the depth of the solvent.

With this arrangement, the chromatographic run is programmed as shown at step 124. For example, a gradient may be programmed into the controller 18 (FIG. 1) to draw one selected fluid from one reservoir and supply it to a mixer together with another solvent from another reservoir, typically with the strongest solvent starting at zero and the weakest solvent starting at 100% and then gradually increasing the stronger solvent and decreasing the weaker solvent to maintain the total flow equal. The timing of the mixture is programmed in accordance with the separation to be performed.

As shown in step 126, as the volume of the solvent in each of the reservoirs is supplied to the chromatographic system, the volume left in the reservoir is measured. This measurement may be accomplished in several different ways. In a preferred embodiment, the change in pressure with respect to the volume of solvent supplied to the columns during the chromatographic run is determined by measuring the pressure at several points during the run. This rate of change of pressure with respect to volume of solvent can be used to predict when the level when the reservoir will run out of solvent, which corresponds to zero pressure, or when it will reach a value preset by the operator to stop the run or provide a message to the operator or automatically supply more solvent to the reservoir. The pressure measured at any point minus the product of the rate of decrease of the pressure per unit of solvent supplied to the columns and the amount of solvent that will be supplied to the columns as programmed in the chromatographic run provides an indication of how close to zero pressure which is an empty reservoir the system will be at any point in the run. Thus a signal indicating a low level of solvent can be given when needed without knowing the exact amount of solvent is in the reservoir at the start of the run.

Of course the signal can be generated in other ways such as by filling the reservoir to a predetermined level and measuring the amount of solvent that is being supplied to the columns by measuring the change in pressure. The amount of the solvent is programmed and the sensor can determine the change in pressure in the reservoirs. From these determinations, based on a change from maximum pressure to a zero pressure, the curve indicating the drop with respect to solvent used indicates the amount of solvent left in a manner independent of the density of the solvent and the shape of the container. On the other hand, the system may be programmed to take into account the density of the liquid and thus indicate the height of the liquid, and the shape of the container can be programmed so as to easily calculate the amount of solvent that is left in the reservoir.

As shown at step 128, when the solvent reaches a generally low level, a low volume indicator signal may be generated to stop the system. Also, as the solvent is depleted, the controller can generate an indication of the amount of solvent left and indicate the amount of solvent to the operator. Thus, as shown at step 130, the chromatograph may be automatically stopped so as to avoid ruining the column and the run until an operator can replenish the reservoir. In the alternative, the solvent level indicating signal can be used to automatically open a valve to a master source of solvent so that the solvent can replenish the reservoirs.

Figure 4:
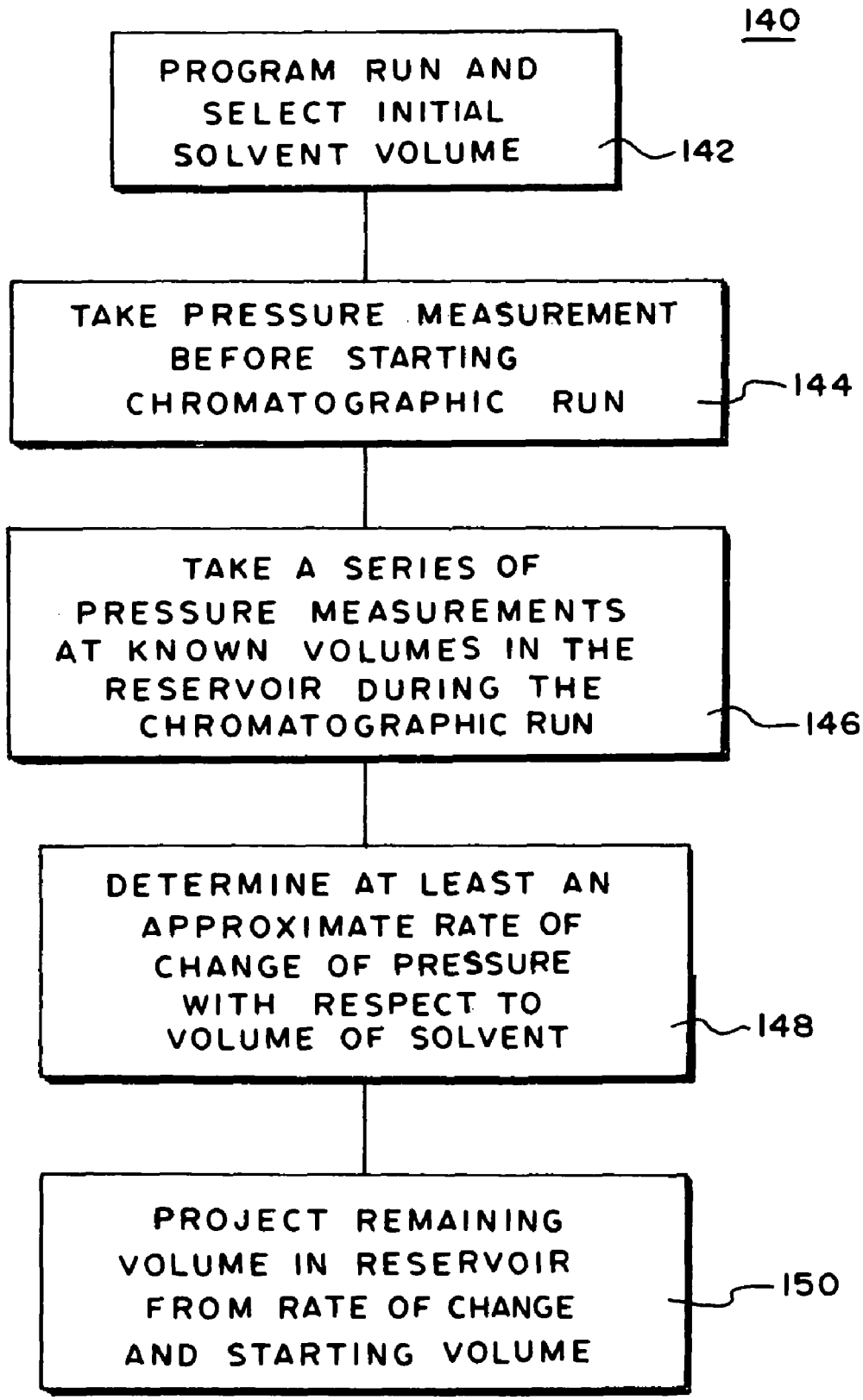
FIG. 4 is a flow diagram of a program for determining the solvent volume indicating a signal in a manner independent of the density of solvent and the shape of the reservoir used in the embodiment of FIG. 1.

In FIG. 4, there is shown a flow diagram of a program 140 for determining the solvent volume indicating signal in a manner independent of the density of the solvent and the shape of the reservoir. As shown in flow diagram 140, a volume of solvent is supplied to the reservoir. A pressure measurement is taken before the chromatographic run so as to obtain a signal indicating the total amount of solvent in the reservoir as shown as step 144. As shown at step 146, a series of pressure measurements at known volumes in the reservoir during the chromatographic run are taken as the program proceeds and each of these steps is correlated with the programmed amount of solvent to be supplied from the reservoir. As shown in step 148, at least an approximate rate of change of pressure is determined with respect to the volume of solvent. As shown in step 150, the remaining volume of solvent in the reservoir is projected from the rate of change of said starting volume. This succession of steps and progress through the program indicates a rate of use of the solvent with respect to the stage of the chromatographic run so as to be able to predict when a low volume of solvent will be left. At that point in time, a low solvent signal may be provided to inform the operator that the solvent is low. The stage of the chromatographic run may be determined in either of terms of volume or in terms of time of the run. In the preferred embodiment, it is determined in terms of volume and the read-out with peaks is correlated with the volume of fluid that has flown through the column. The starting solvent minus the rate of change of pressure with respect to time or volume programmed multiplied by the starting volume in the run indicates the amount of solvent left.

It can be understood from the above description that the liquid chromatographic apparatus and technique of this invention has several advantages, such as: (1) it avoids having solvent run out during a chromatographic run, resulting in wasted solvent, a compromised column, lost sample and/or lost operator time; (2) it reduces the monitoring effort that must be supplied by persons operating the chromatograph; and (3) it is relatively inexpensive and can be implemented principally as software.

Although a preferred embodiment of the invention has been described with some particularity, it is to be understood that the invention may be practiced other than as specifically described. Accordingly, it is to be understood that, within the scope of the appended claims, the invention may be practiced other than as specifically described.

What is claimed is:

1. Apparatus for performing liquid chromatography comprising:
   at least one solvent reservoir;
   a liquid chromatographic system including a microcontroller;
   a depth measuring instrument within said at least one solvent reservoir for generating a depth signal;
   said solvent depth measuring instrument being connected to the microcontroller whereby the microcontroller is configured for:
   1) receiving the depth signal;
   2) indicating when the depth of the solvent is low;
   3) receiving and storing at least one parameter, the at least one parameter defining an amount of a solvent required from the at least one solvent reservoir for a corresponding chromatographic run;
   4) determining a rate of change of the depth signal with respect to the at least one parameter;
   5) directing a replenishment of the at least one solvent reservoir when the determining predicts a possible exhaustion of the solvent; and
   6) terminating a chromatographic run when the determining predicts a possible exhaustion of the solvent.

2. A liquid chromatographic system in accordance with claim 1 in which the depth measuring instrument is a pressure sensor compatible with solvent in the at least one solvent reservoir.

3. A liquid chromatographic system in accordance with claim 2 in which the pressure sensor is a bubbler.

4. A liquid chromatographic system in accordance with claim 2 in which the depth measuring instrument includes a sensing means inserted at the bottom of the at least one solvent reservoir within the solvent.

5. A liquid chromatographic system in accordance with claim 2 in which there are at least two reservoirs including different solvents, each reservoir including a pressure sensor within it.

6. A liquid chromatographic system in accordance with claim 5 in which a pressure signal is obtained and supplied to a microprocessor, said microprocessor including program means for determining the level of solvent from the depth signal.

7. A liquid chromatographic system in accordance with claim 2 further including means for terminating a chromatographic run when said depth signal indicates the solvent is below a predetermined level.

8. A liquid chromatographic system in accordance with claim 1 in which said microcontroller includes a display means, said display means including a display for indicating the amount of solvent remaining in the at least one solvent reservoir.

* * * * *